United States Patent
Ford et al.

[11] Patent Number: 6,095,572
[45] Date of Patent: Aug. 1, 2000

[54] QUARTER TURN QUICK CONNECT FITTING

[75] Inventors: Douglas W. Ford, West Linn, Oreg.; Derrick S. Levanen, Hancock, Mich.; John T. Martin, Portland, Oreg.

[73] Assignee: Optimize Technologies, Inc., Oregon City, Oreg.

[21] Appl. No.: 09/009,647

[22] Filed: Jan. 20, 1998

[51] Int. Cl.[7] .................................................. F16L 17/06
[52] U.S. Cl. ......................................... 285/361; 210/198.2
[58] Field of Search ....................................... 285/325, 327, 285/361, 376, 402; 210/198.2; 277/608

[56] References Cited

U.S. PATENT DOCUMENTS

| | | | |
|---|---|---|---|
| 626,932 | 6/1899 | Reed et al. | ............................. 285/361 X |
| 796,306 | 8/1905 | Exley . | |
| 1,724,822 | 8/1929 | Brown . | |
| 1,885,321 | 11/1932 | Benn . | |
| 2,204,392 | 6/1940 | Arm | ...................................... 285/379 X |
| 2,349,081 | 5/1944 | Douglass . | |
| 3,045,857 | 7/1962 | Lineweber | ............................ 277/608 X |
| 3,820,571 | 6/1974 | Grier | ...................................... 277/608 X |
| 3,877,732 | 4/1975 | Mohaupt . | |
| 4,283,280 | 8/1981 | Brownlee . | |
| 4,313,828 | 2/1982 | Brownlee . | |
| 4,451,364 | 5/1984 | Higgins et al. . | |
| 4,586,732 | 5/1986 | Anderson, Jr. . | |
| 4,587,014 | 5/1986 | America . | |
| 4,632,433 | 12/1986 | Kimura | ................................ 285/361 X |
| 4,648,635 | 3/1987 | Juhling . | |
| 4,737,284 | 4/1988 | Hauke et al. . | |
| 4,842,592 | 6/1989 | Caggiani et al. . | |
| 4,876,005 | 10/1989 | America . | |
| 5,016,920 | 5/1991 | Anderson . | |
| 5,087,086 | 2/1992 | Snedeker | ................................. 285/361 |
| 5,194,225 | 3/1993 | Müller et al. . | |
| 5,299,842 | 4/1994 | Marks et al. | ............................ 285/325 |
| 5,472,598 | 12/1995 | Schick . | |
| 5,540,464 | 7/1996 | Picha . | |
| 5,601,785 | 2/1997 | Higdon | ............................. 210/198.2 X |

FOREIGN PATENT DOCUMENTS

| | | | |
|---|---|---|---|
| 1220111 | 5/1960 | France | ................................... 285/361 |

*Primary Examiner*—Lynne H. Browne
*Assistant Examiner*—Greg Binda
*Attorney, Agent, or Firm*—Christensen O'Connor; Johnson & Kindness PLLC

[57] ABSTRACT

A quarter turn quick connect fitting assembly (10) for connecting miniature fluid conduits, such as tubing, includes a first fitting (12) having radially projecting pins (28) and a second fitting (14) located within a rotatable quarter turn nut (16) having spiral grooves (48) which receive the pins. The first fitting defines a central passage (26) and the second fitting defines a central passage (42) which may each be configured to slidably receive a hollow tube set (104), or to threadably receive an externally threaded mating fitting. The quarter turn quick connect fitting can be configured to attach to the end of a column, and can include an adapter (158), which houses a guard column (160), or a frit (188) for filtering the fluid passing through the quarter turn quick connect fitting assembly. The quarter turn quick connect fitting is assembled by sliding the pins of the first fitting into the grooves of the quarter turn nut and rotating the quarter turn nut through approximately 90° with respect to the first fitting, thereby securely seating the pins within angled areas defined at the ends of the grooves.

37 Claims, 8 Drawing Sheets

6,095,572

QUARTER TURN QUICK CONNECT FITTING

FIELD OF THE INVENTION

The present invention relates to fittings used to connect miniature fluid conduits, and especially fittings used to connect miniature fluid conduits utilized in liquid chromatography.

BACKGROUND OF THE INVENTION

Numerous types of equipment used for the analysis or purification of chemical compounds utilize miniature fluid conduits, such as metallic tubing, within which liquid samples pass through the system. For example, liquid chromatography is a technique in which a column is packed with a packing material, an analyte is introduced into one end of the column, and a carrier fluid is then run through the column. The length of time that the analyte is retained within the column can enable analysis and identification of the analyte. A popular form of liquid chromatography is High Performance Liquid Chromatography (HPLC) in which the sample is pumped through the column under an elevated pressure, typically at 300 to 6,000 psi.

Liquid chromatography systems, such as HPLC systems, typically include several components, for example; a pump; an injection valve for injecting the analyte; a precolumn filter to remove particulate matter in the analyte solution that might clog the column; a guard column to retain irreversibly adsorbed chemical material; the HPLC column itself; and a detector that analyzes the carrier fluid as it leaves the column. These various components may typically be connected by a miniature fluid conduit, such as metallic or polymeric tubing, usually having an internal diameter of 0.005 to 0.040 inch. All of these various components and lengths of tubing are typically interconnected by threaded fittings. Often, a first internally threaded fitting seals to a first component with a ferrule or similar sealing device. The first fitting is threadedly connected through multiple turns by hand or by use of a wrench or wrenches to a second fitting having a corresponding external fitting, which is in turn sealed to a second component by a ferrule or other seal. Disconnection of these fittings for component replacement, maintenance or reconfiguration again requires the use of a wrench or wrenches to unthread the fittings. Most thread connections are 10-32, ¼-28 or 6 mm×1. If a hand-tightened threaded fitting is used, it may not stand up to the extreme pressures of HPLC.

SUMMARY OF THE INVENTION

The present invention provides a quick connect fitting assembly for coupling first and second analytical fluid conduits. The assembly includes a first fitting defining a central passage for receiving the first fluid conduit therein, the first fitting defining at least one first radial engaging surface, and a second fitting defining a central passage for receiving the second fluid conduit therein. The assembly further includes an annular nut rotatably mounted on the second fitting, wherein the nut defines at least one second radial engaging surface, wherein the nut is selectively rotatable less than 360° relative to the first fitting to engage the first and second engaging surfaces to create a secure seal between the first and second fittings for fluid flow communication between the first and second fluid conduits.

A preferred embodiment of the present invention provides a quarter turn quick connect fitting assembly, including a first fitting having radially projecting connecting protrusions and a second fitting having grooves which receive the connecting elements, which is operable by twisting one of the components by less than a full turn, preferably by a ¼ turn. Both the first and second fittings define a central passage which may be configured to slidably receive a hollow tube, or which may be internally threaded to threadedly receive an externally threaded mating fitting. The first and second fittings are selectively connected by sliding the connecting elements of the first fitting into the grooves of the second fitting and rotating the quarter turn nut through approximately 90° with respect to the first fitting. The connecting elements are thereby securely seated within angled areas at the inner ends of the grooves.

In a first preferred embodiment of the quarter turn quick connect fitting, the first fitting includes a body having a proximal end and a distal end. Two pins radially project from the distal end of the first fitting. The body of the first fitting defines a central passage extending from the proximal end of the first fitting to a centrally located recess on the distal end of the first fitting. The central passage can be configured to slidably receive a hollow tube set, or to threadedly receive an externally-threaded mating fitting. The second fitting includes a body having a proximal end and a distal end. A central passage extends from the proximal end of the first fitting to a centrally-located recess on the distal end of the first fitting. The central passage can be configured to slidably receive a hollow tube set, or to threadably receive an externally-threaded mating fitting. The second fitting is mounted within a rotatable nut, and is biased therein by at least one spring washer. The rotatable nut has a proximal end and a distal end, and includes two spiral grooves which open onto the distal end of the nut. The two spiral grooves receive the two dowel pins of the first fitting, thereby coupling the first fitting to the quarter turn nut, as set forth above. A compressible sealing element, having a body defining a central passage, is located between the first and second fittings and forms a seal when the first and second fittings are locked together. The central passages of the first fitting, the sealing element and the second fitting thus form a continuous, sealed passage within which there is no deadspace to reduce or interrupt fluid flow therein, or cause band broadening of the analyte sample.

A second preferred embodiment of the present invention is similar to the first preferred embodiment, except that the central passage of the first fitting is beveled at the proximal end and is configured to slidably receive an HPLC column end fitting. The first fitting is externally threaded and is retained on the column end by means of an internally threaded nut mounted coaxially around the HPLC column end fitting and which is screwably attached to the externally threaded surface of the first fitting. A seal is formed between the beveled surface of the central passage of the first fitting and a ferrule mounted coaxially around the HPLC column end fitting.

A third preferred embodiment of the present invention is similar to the first preferred embodiment, except that the central passage of the first fitting is internally threaded to receive the externally threaded end of a HPLC column.

In a fourth preferred embodiment of the present invention, the quarter turn quick connect fitting includes a first fitting having a central passage internally threaded to receive a HPLC column end fitting, as described for the third preferred embodiment, and a second fitting located within a quarter turn nut. The fourth preferred embodiment of the present invention further includes an adapter having a body defining a central passage. The adapter body has a proximal end and a distal end, the proximal end having two grooves and the distal end having two radially projecting dowel pins. The central passage of the adapter is configured to receive a guard column. The first fitting is connected to the adapter by rotatably inserting the dowel pins of the first fitting into the grooves of the proximal end of the adapter. The second fitting is connected to the adapter by rotatably inserting the dowel pins of the distal end of the adapter into the grooves of the distal end of the quarter turn nut.

In a fifth preferred embodiment, the quarter turn quick connect fitting includes a first fitting, a second fitting located within a quarter turn nut, and a frit composed of a sintered material that filters the fluid passing therethrough. The frit is housed within a frit ring composed of a deformable material that forms a seal between the first and second fitting within the quarter turn quick connect fitting.

Additionally, the second fitting in any of the foregoing preferred embodiments can include a slot extending from the proximal end to the distal end of the second fitting, and completely penetrating one side of the second fitting body. The slot within the second fitting body permits the hollow tube set to be readily disconnected from the second fitting by withdrawing the second fitting from the quarter turn nut cavity and sliding the hollow tube set laterally through the groove in the second fitting body. When the embodiment of the second fitting including a slot is utilized, the second fitting is not fixedly retained within the quarter turn nut. Instead, a retaining ring within the quarter turn nut cavity retains the spring washers. The retaining ring is seated within an annular groove disposed around the circumference of the quarter turn nut cavity. The embodiment of the quarter turn nut having the annular groove can be used with any of the foregoing embodiments of the quarter turn quick connect fitting. Rather than slotting the second fitting, the first fitting can be slotted.

Thus, the present invention provides a quarter turn quick connect fitting for rapidly and easily connecting miniature fluid conduits without creating any deadspace therebetween. Connection is made by a single hand motion, preferably by rotating the fittings relative to each other through a single hand motion without need for changing grip, still more preferably by rotating through no more than 360 degrees, and most preferably by rotating through only a ¼ turn. A quick connection is thus provided, as compared to the time consuming connection of a conventional, fully threaded connection. During mating of the fittings and after mating, the tubes or other components are axially retained by the first and second fittings acting on positive stops defined by the tubes or associated hardware. The quarter turn quick connect fitting can include one or more frits, screens, or additional stationary phase packing material, such as C18, Silica, etc., for filtering, conditioning or retaining analyte from the fluid passing therethrough. Further, the seal formed within the quick connect fitting will hold when fluid is pumped at high pressure through the assembled quick connect fitting.

The present invention thus provides for the quick and easy connection and disconnection of miniature fluid conduits and fittings that join the components of a liquid chromatography system, or other chemical analytical equipment, so that, for example, the system can be rapidly reconfigured to perform a different type of analysis. The operation of the quick connect fittings of the present invention require only the use of normal manual strength and dexterity, and do not require the use of special tools. Connection and disconnection is provided by a simple ¼ turn, with the ¼ turn serving as a retainer member for the first and second fittings. The quick connect fittings of the present invention are able to hold a seal under the relatively high pressures often utilized in liquid chemical analytical systems, such as an HPLC system. Additionally, the quick connect fittings of the present invention do not create any dead volume, i.e., space in which the flow of the analyte would be reduced or interrupted, which would permit the flowing analyte to stagnate and its partially or completely separated components to mix.

BRIEF DESCRIPTION OF THE DRAWINGS

The foregoing aspects and many of the attendant advantages of this invention will become better understood by reference to the following detailed description, when taken in conjunction with the accompanying drawings, wherein.

DETAILED DESCRIPTION OF THE PREFERRED EMBODIMENT

Figure 1:
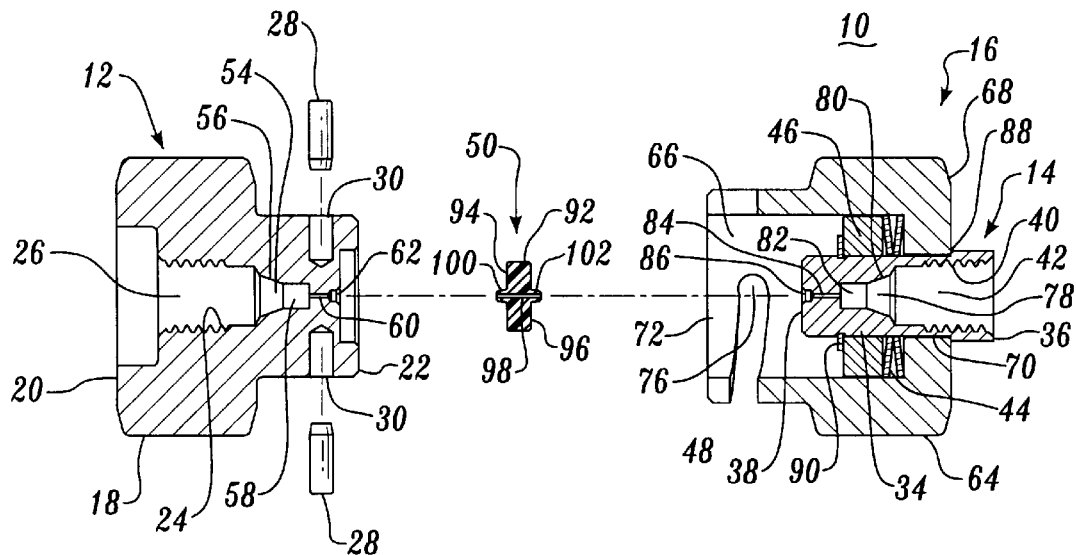
FIG. 1 is a longitudinal cross-sectional exploded view of a first configuration of a first preferred embodiment of the quarter turn quick connect fitting of the present invention.

A first preferred embodiment of a quarter turn quick connect fitting assembly 10 constructed in accordance with the present invention is shown in FIG. 1. The quarter turn quick connect fitting assembly 10 includes a first fitting 12 and a second fitting 14 on which is rotatably secured a quarter turn nut 16. First fitting 12 includes a tubular body 18 having a proximal end 20 and a distal end 22. A central passage 26 extends from proximal end 20 to distal end 22 of body 18. The proximal end of central passage 26 has an internally threaded surface 24. Two radially projecting pins 28 are located within two diametrically opposed radial passages 30 close to the distal end 22 of body 18.

Second fitting 14 includes a tubular body 34 having a proximal end 36 and a distal end 38. A central passage 42 extends from proximal end 36 to distal end 38 of body 34. The proximal end of central passage 42 has an internally threaded surface 40. Second fitting 14 is rotatably received within quarter turn nut 16, and is supported therein by two spring washers 44 and a support washer 46. Quarter turn nut 16 includes two spiral grooves 48 formed through the annular wall thereof, which selectively receive dowel pins 28 of first fitting 12 for mating of the first and second fitting. Quarter turn nut 16 and first fitting 12 are selectively locked together by inserting dowel pins 28 into spiral grooves 48 and rotating quarter turn nut 16 through approximately 90° with respect to first fitting 12. When quarter turn nut 16 and first fitting 12 are locked together, a seal is formed between first fitting 12 and second fitting 14 by means of a sealing element 50 captured therebetween.

Figure 2:
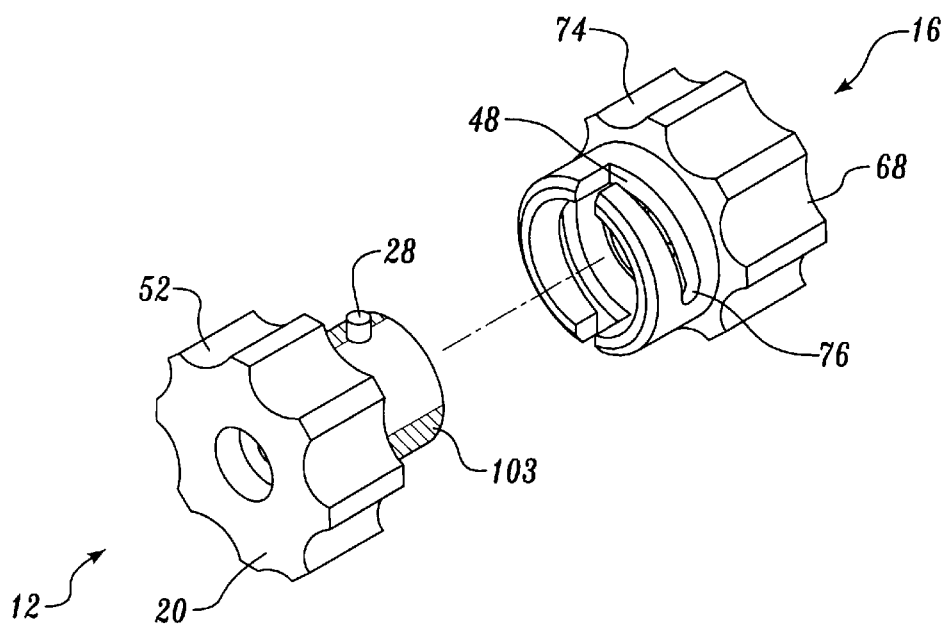
FIG. 2 is an isometric view of the unmated first and second fittings of FIG. 1.
Figure 11:
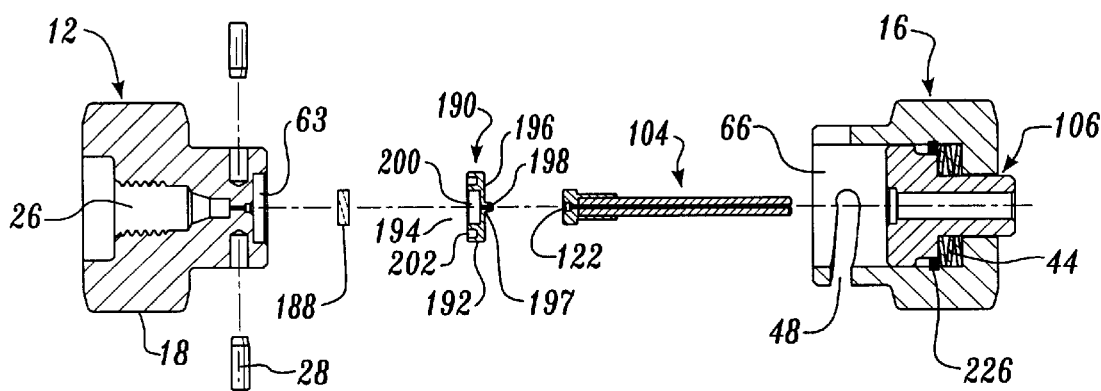
FIG. 11 is a longitudinal cross-sectional exploded view of a first configuration of a fifth preferred embodiment of the quarter turn quick connect fitting of the present invention including a frit and a frit ring having a grooved sealing surface.

With reference again to FIG. 1, the first fitting 12 will now be described in greater detail. First fitting body 18 is preferably of unitary construction and has an overall tubular configuration, with the diameter of proximal end 20 being greater than the diameter of distal end 22. Proximal end 20 of first fitting 12 preferably has a knurled outer surface 52 to facilitate gripping and turning first fitting 12, as shown more clearly in FIG. 2. Pins 28, when inserted into the radial passages 30 in the distal end 22, project radially from distal end 22. The internally threaded portion 24 of central passage 26 is designed for receiving an externally threaded mating coupling of a miniature fluid conduit (not shown). The internally threaded portion 24 of central passage 26 narrows in diameter at its distal terminus to form a tapered chamber 54, which extends from internally threaded portion 24 towards distal end 22 of first fitting 12. Tapered chamber 54 has a frustoconical sealing surface 56 that seals against a conventional ferrule (not shown) received coaxially on the miniature fluid conduit (not shown). Tapered chamber 54 further narrows to form a cylindrical chamber 58 which extends from tapered chamber 54 into distal end 22 of first fitting 12. Cylindrical chamber 58 forms a "tube stop" that closely and fully receives the distal tip of the miniature fluid conduit. Cylindrical chamber 58 further narrows to form a small diameter passage 60 extending from cylindrical chamber 58 to a centrally-located sealing recess 62 within a larger annular recess 63 (as shown in FIG. 11) on the distal surface of first fitting distal end 22. The passage 60 is sized to correspond to the internal diameter of the fluid conduit, for a zero-dead volume connection.

Again with reference to FIG. 1, quarter turn nut 16 is preferably of unitary construction, having a tubular body 64, defining a cavity 66 therein, a closed proximal end 68, penetrated by a centrally located hole 70, and an open distal end 72. The outer surface 74 of body 64 is preferably knurled close to proximal end 68 to facilitate gripping and turning of quarter turn nut 16, as shown more clearly in FIG. 2. Distal end 72 of quarter turn nut body 64 is narrower in diameter than proximal end 68 and is penetrated by first and second opposed spiral grooves 48, as more clearly shown in FIG. 2. Each spiral groove 48 opens out onto the distal edge of body 64, and extends helically towards the proximal end turning approximately 90° of travel. The proximal terminus of each groove 48 terminates in an enlarged or oppositely angled area 76 that bends slightly back towards the distal tip of the body 64, to provide a positive "snap" locking engagement of the pins 28 upon mating.

Note that while the grooves 48 are shown as passing completely through the wall of the nut 16, they could instead, by way of non-limiting example, be formed only on the inner surface of the nut. Further, while pins 28 are shown mounted on first fitting 12 and grooves 48 are shown formed in the nut 16, they could be inversely configured, with the pins projecting inwardly into the nut 16 to engage grooves formed on the exterior of fitting 12. Additionally, rather than using locking portions of grooves 48, first fitting 12 can be reversibly locked to quarter turn nut 16 by means of a spring-loaded ball (not shown) housed within and projecting partially from first fitting body 18 and which engages a complementary recess (not shown) in the portion of quarter turn nut body 64 defining quarter turn nut cavity 66. When the nut body 64 is rotated fully with respect to first fitting 12, the ball aligns with and loads into the recess. This engagement maintains the components locked against accidental disengagement.

Fitting assembly 10 has been described in terms of the nut 16 and second fitting 14 as separate pieces. However, it should be apparent based on the disclosure contained herein that the nut and second fitting could instead be integrally formed for those applications in which the tubular conduit associated with the second fitting can be rotated with the nut without damage. This same adaptation can be made to the various other embodiments of the invention described herein.

With reference again to FIG. 1, second fitting 14 is of unitary construction and has a generally cylindrical shape. Central passage 42 has an internally threaded portion 40 defined through the length of proximal end 36 of body 34. The internally threaded portion 40 of central passage 42 is designed for receiving an externally threaded mating coupling of a miniature fluid conduit (not shown). Central passage 42 narrows in diameter to form a tapered chamber 78, which extends from internally threaded portion 40 into distal end 38 of second fitting 14. Tapered chamber 78 has a frustoconical sealing surface 80 for sealing against a ferrule (not shown) included on the miniature fluid conduit.

Tapered chamber 78 further narrows to form a cylindrical tube stop chamber 82 which extends from tapered chamber 78 into distal end 38 of second fitting 14. Cylindrical chamber 82 further narrows to form a small diameter passage 84 extending from cylindrical chamber 82 to a centrally-located seal recess 86 on the distal surface of second fitting distal end 38, which again is dimensioned for a zero-dead volume connection.

The proximal end of second fitting 14 is inserted into quarter turn nut cavity 66 through hole 70 in proximal end 68 of quarter turn nut 16, so that the distal end of second fitting 14 is surrounded by the nut 16. A shoulder 88 on the outer surface of second fitting body 34 limits the penetration of second fitting 14 into quarter turn nut cavity 66 so that proximal end 36 of second fitting 14 is located substantially exterior of quarter turn nut body 64. Second fitting 14 is biased within quarter turn nut cavity 66 by one or more spring washers 44, preferably a stack of oppositely oriented spring washers, which are coaxially disposed around second fitting body 34 within quarter turn nut cavity 66. Additionally, second fitting 14 is supported within quarter turn nut cavity 66 by means of an annular support washer 46 which is coaxially disposed around second fitting body 34 on the distal side of the spring washers 44. Spring washers 44 and support washer 46 are retained within quarter turn nut cavity 66 by means of a spring clip type retaining ring 90 which fits over distal end 38 of second fitting 14 and is received within an annular groove formed thereon. When the retaining ring 90 is installed, the spring washers 44 are partially compressed, which acts to bias second fitting 14 in the distal direction to seal against first fitting 12. The spring washers 44 ensure a compressive seal on sealing element 50, even if components of fitting assembly 10 wear during repeated matings and unmatings.

Again with respect to FIG. 1, sealing element 50 is formed from an elastically deformable polymeric elastomer includes a substantially annular body 92 having a first face 94 and a second face 96. Sealing element body 92 defines a central passage 98 extending from a centrally-located nipple 100 on sealing element first face 94 to a centrally-located nipple 102 on sealing element second face 96. When first fitting 12 is connected to second fitting 14, by securely seating pins 28 within angled areas 76 of grooves 48 of quarter turn nut 16, nipple 100 on sealing element first face 94 is compressed into sealing recess 62 of first fitting distal end 22, and nipple 102 on sealing element second face 96 is compressed into sealing recess 86 of second fitting distal end 38, thereby forming a seal between first fitting distal end 22 and second fitting distal end 38. The central passage 98 is dimensioned to match the external diameter of the miniature fluid conduit (e.g., tube) and of first and second fittings 12 and 14, and no discontinuities are presented, so that a complete zero-dead volume junction is made from tube to tube.

Figure 3:
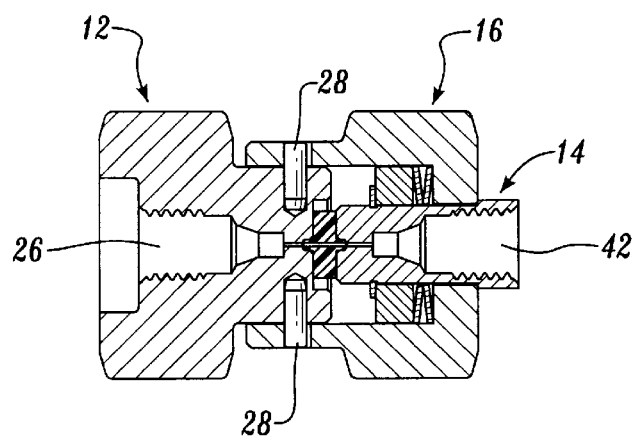
FIG. 3 is a longitudinal cross-sectional view of the assembled first and second fittings of FIG. 1.

The first preferred embodiment of quarter turn quick connect fitting 10 is shown in the assembled configuration in FIG. 3. When quarter turn quick connect fitting 10 is assembled, central passage 26 of first fitting 12, central passage 98 of sealing element 50 and central passage 42 of second fitting 14, together form a continuous, sealed passage within which there is no deadspace to reduce or interrupt fluid flow through quarter turn quick connect fitting 10. Further, assembled quarter turn quick connect fitting 10 is capable of holding a seal under the high pressures used to operate certain chemical analytical devices, for example an HPLC column and system. Quarter turn quick connect fitting 10 of the present invention preferably operates without liquid leakage under pressures in the range 300 to 20,000 psi, most preferably in the range 500 to 6000 psi.

With the passage of time the components of quarter turn quick connect fitting 10, in particular pins 28 and the surfaces in grooves 48 which they contact, will tend to wear. Spring washers 44 serve to ensure that component wear does not reduce the tightness of the quarter turn quick connect fitting 10 coupling. Spring washers 44 are compressed when quarter turn nut quick connect fitting 10 is assembled, and exert a resistive force against second fitting 14 which ensures that pins 28 continue to be tightly held within grooves 48, thereby maintaining the integrity of the seal within quarter turn quick connect fitting 10.

Surface indicia may be applied to body 18 of first fitting 12 in order to aid the user of the present invention to determine when pins 28 are securely seated within angled areas 76 of grooves 48. By way of non-limiting example, the surface of the distal end of first fitting body 18 may be divided into quadrants 103 which are alternately painted red and green so that when pins 28 are securely seated within enlarged areas 76 of grooves 48, only a green quadrant of first fitting 12 is visible through grooves 48. Conversely, a red segment is exposed if the connectors are not fully seated.

While the first preferred embodiment of quarter turn quick connect fitting assembly 10, shown in FIG. 1, includes first fitting 12 and second fitting 14 each internally threaded to receive an externally threaded mating coupling of a miniature fluid conduit, either or both of first fitting 12 and second fitting 14 can be configured to receive or engage with a broad variety of other conduit terminals. For example, either or both fittings could be externally threaded, or could be configured to receive a polymeric sleeved fitting such as that disclosed in U.S. Pat. No. 5,669,637 to Martin et al., the disclosure of which is hereby expressly incorporated by reference.

Figure 4:
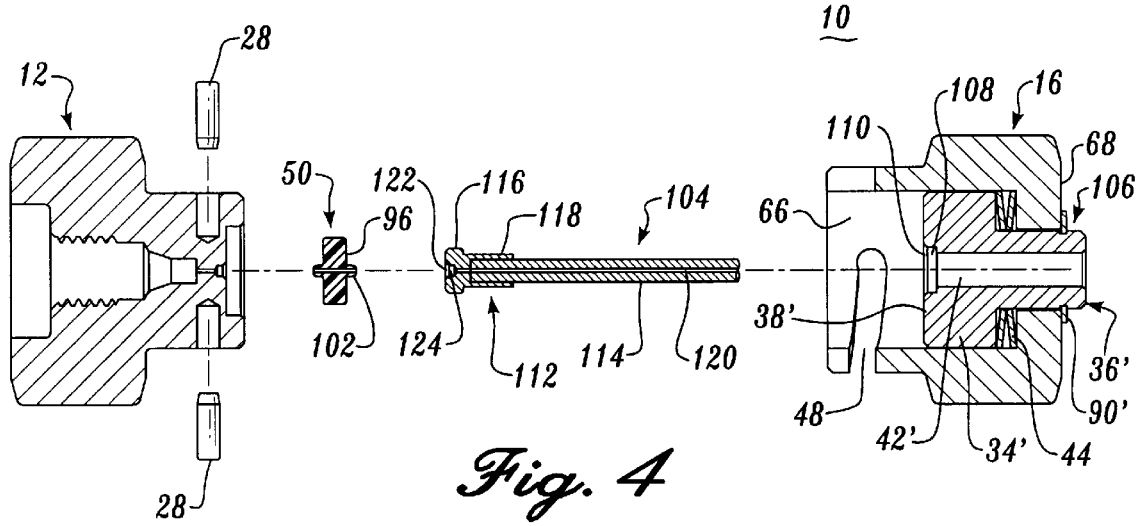
FIG. 4 is a longitudinal cross-sectional exploded view of a second configuration of the first preferred embodiment of the quarter turn quick connect fitting of the present invention.
Figure 5:
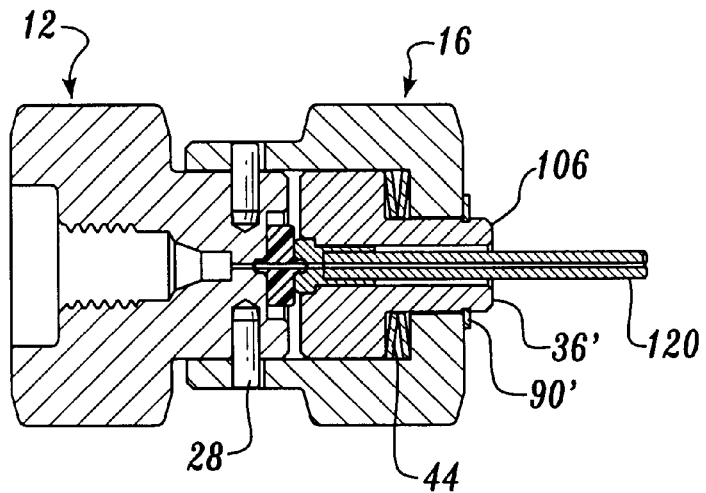
FIG. 5 is a longitudinal cross-sectional view of the assembled second configuration of the first preferred embodiment of FIG. 4.
Figure 6:
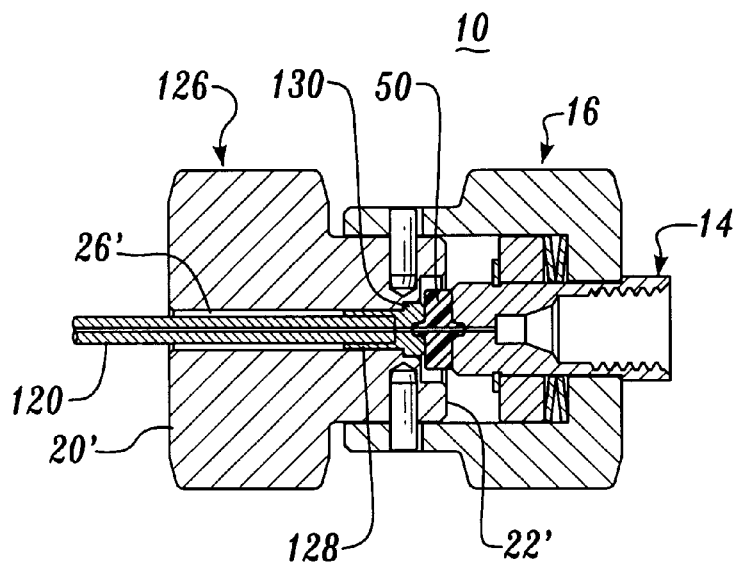
FIG. 6 is a longitudinal cross-sectional view of an assembled third configuration of the first preferred embodiment of the quarter turn quick connect fitting of the present invention.

Three possible alternate configurations of the embodiment of FIG. 1 adapted for use with another style of hollow tube set are shown in FIGS. 4–6. Initially, FIG. 4 shows a configuration of the first preferred embodiment of quarter turn quick connect fitting assembly 10 in which first fitting 12, sealing element 50 and quarter turn nut 16 are as previously described, but a second fitting 106 is configured to receive a hollow tube set 104. Corresponding features of second fitting 106 are referred to with the same parts numbers as second fitting 14, but with the addition of a prime ('). Second fitting 106 includes a unitary body 34' of generally cylindrical shape and having a proximal end 36' and a distal end 38', proximal end 36' being narrower than distal end 38'. Second fitting body 34' defines a central passage 42' extending from proximal end 36' to distal end 38'. Central passage 42' is of uniform diameter, except that it widens in the portion of distal end 38' furthermost from proximal end 36'. As central passage 42' widens, close to distal end 38,' it forms a first annular portion 108 and then a second annular portion 110, second annular portion 110 being wider in diameter than first annular portion 108.

Second fitting 106 is configured to receive hollow tube set 104 which includes a head 112 and a hollow tube 114. Head 112 includes an annular, disk shaped head portion 116 and a tubular stem 118, which extends longitudinally from the center of head portion 116 and has a smaller diameter than head portion 116. One end of tube 114 is inserted into stem 118, which is sized to closely receive hollow tube 114, and is secured therein by standard means, such as soldering or swaging. Alternatively, stem 118 can be internally-threaded and threadably attached to an externally-threaded end of hollow tube 114. Hollow tube set 104 defines a central passage 120 which extends throughout the length of hollow tube set 104 and is of uniform diameter, except that central passage 120 widens within head 112 to form a centrally-located sealing recess 122 on the distal end of head portion 116. Sealing recess 122 forms a frustoconical sealing surface 124.

Hollow tube 114 of hollow tube set 104 is inserted into the distal end of central passage 42' of second fitting 106 until stem 118 is received by first annular portion 108 of central passage 42', and flattened head portion 116 is received by second annular portion 110 of central passage 42'. When hollow tube set 104 is fully inserted into central passage 42', the end of hollow tube 114 furthermost from head 112 projects beyond the proximal end 36' of second fitting 106.

Second fitting 106 is disposed and retained within quarter turn nut cavity 66 as previously described, except that support washer 46 is not required to immobilize second fitting 106 within quarter turn nut cavity 66. Also, second fitting 106 and spring washers 44 are retained within quarter turn nut cavity 66 by retaining ring 90' coaxially mounted over proximal end 36' of second fitting 106, that protrudes beyond proximal end 68 of quarter turn nut 16.

Connection of first fitting 12 to second fitting 106 is achieved as previously described. When first fitting 12 is connected to quarter turn nut 16, by locking pins 28 into position within grooves 48 of quarter turn nut 16, nipple 100 on sealing element first face 94 is compressed into sealing recess 62 of first fitting distal end 22, and nipple 102 on sealing element second face 96 is compressed into sealing recess 122 of flattened head portion 116, thereby forming a seal between first fitting distal end 22 and flattened head portion 116. The assembled quarter turn quick connect fitting 10 including second fitting 106 is shown in FIG. 5.

FIG. 6 shows an assembled third configuration of the first preferred embodiment of quarter turn quick connect fitting assembly 10, including a second fitting 14, a quarter turn nut 16 and a sealing element 50 as previously described for the first configuration of the first preferred embodiment of the present invention, but having a first fitting 126 configured to receive a hollow tube set 104. Corresponding features of first fitting 126 are referred to with the same parts numbers as first fitting 12, but with the addition of a prime ('). First fitting 126 is identical to previously described first fitting 12, except for the configuration of central passage 26'. Central passage 26' is of uniform diameter, except that it widens in the portion of distal end 22' furthermost from proximal end 20'. Central passage 26' thus defines a first annular portion 128 and then a second annular portion 130, second annular portion 130 being wider in diameter than first annular portion 128.

Hollow tube 114 of hollow tube set 104 is inserted into distal end of central passage 26' of first fitting 126 until stem 118 is received by first annular portion 128 of central passage 26', and head portion 116 is received by second annular portion 130 of central passage 26'. When hollow tube set 104 is fully inserted into central passage 26', the end of hollow tube 114 furthermost from head 112 projects beyond proximal end 20' of first fitting 126. Quarter turn quick connect fitting 10 is then connected as previously described.

Figure 7:
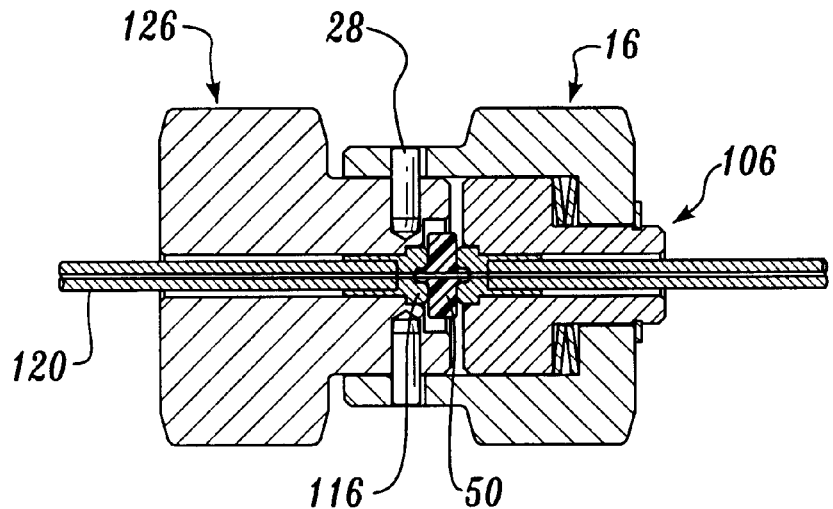
FIG. 7 is a longitudinal cross-sectional view of an assembled fourth configuration of the first preferred embodiment of the quarter turn quick connect fitting of the present invention.

FIG. 7 shows an assembled fourth configuration of the first preferred embodiment of quarter turn quick connect fitting assembly 10, including first fitting 126, second fitting 106, quarter turn nut 16 and sealing element 50. First fitting 126 and second fitting 106 are each configured to receive a hollow tube set 104, as previously illustrated in FIG. 6 and FIG. 4, respectively. As pins 28 of first fitting 126 are locked into position within grooves 48 of quarter turn nut 16, sealing element 50 is compressed between adjacent, head portions 116 of aligned, hollow tube sets 104 and a seal is formed as nipples 100 and 102 are squeezed into sealing recess 122 (as shown in FIG. 4) on head portion 116 of each of the two hollow tube sets 104.

Figure 8:
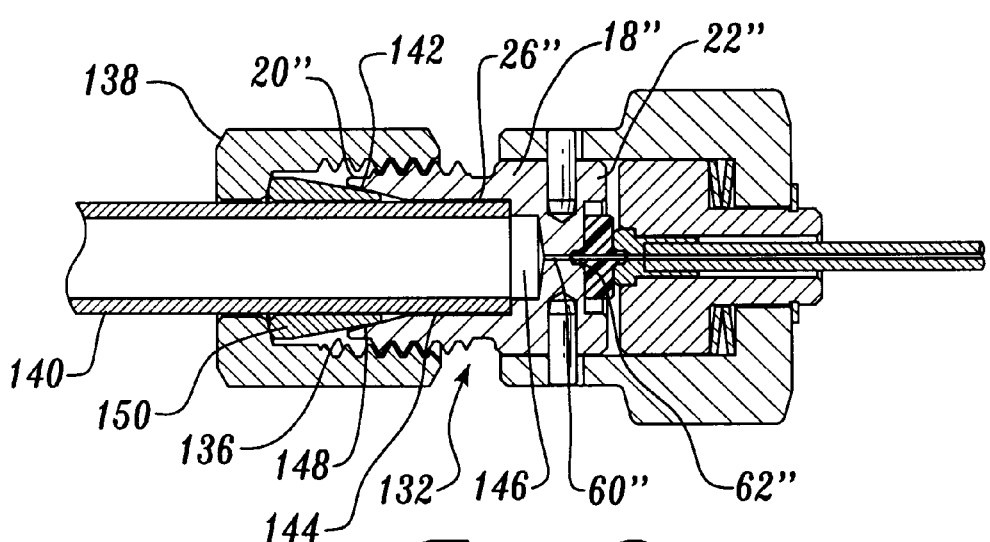
FIG. 8 is a longitudinal cross-sectional view of a second preferred embodiment of the quarter turn quick connect fitting of the present invention adapted for use as a column end fitting slidably fitted over the end of a column and retained thereon by a nut.

Quarter turn nut quick connect fitting assembly 10 of the present invention can also be adapted for use as a column end fitting. FIG. 8 shows a second preferred embodiment of the present invention including a first fitting 132 adapted for use on the end of a HPLC column. Quarter turn nut 16, second fitting 106, hollow tube set 104 and sealing element 50 are as previously described. First fitting 132 is similar to first fitting 12 and so features of first fitting 132 that correspond to features of first fitting 12 are referred to with the same parts numbers as first fitting 12, but with the addition of a double prime ("). Thus, as shown in FIG. 8, first fitting 132 includes a body 18" having a proximal end 20" and a distal end 22". Body 18" defines a central passage 26". First fitting body 18" is of unitary construction and has an overall tubular configuration. Proximal end 20" of body 18" has an externally-threaded surface 134 to engage internally-threaded surface 136 of nut 138, which is coaxially mounted around column end 140. Central passage 26" is beveled to define a sealing surface 142 within proximal end 20" of body 18". Central passage 26" narrows in diameter to form a cylindrical portion 144 extending away from proximal end 20" into body 18". Cylindrical portion 144 extends into body 18" and narrows to form an annular portion 146 which houses a frit (not shown). Annular portion 146 further narrows to form a small diameter passage 60" extending from annular portion 146 to a centrally-located sealing recess 62" on the surface of first fitting distal end 22".

Column end 140 is slidably received by cylindrical portion 144 of central passage 26". A seal is formed between beveled sealing surface 142 of central passage 26" and a complementary beveled surface 148 of a ferrule 150 coaxially mounted around column end 140. First fitting 132 is securely retained on column end 140 by means of internally threaded nut 138 which is threadably attached to externally threaded surface 134 of first fitting 132. First fitting 132 is connected to quarter turn nut 16, and quarter turn nut quick connect fitting 10 thereby assembled, as previously described. It will be appreciated that while the second preferred embodiment of the present invention, illustrated in FIG. 8, includes a second fitting 106 configured to receive a hollow tube set 104, an internally threaded second fitting 14 can instead be utilized.

Figure 9:
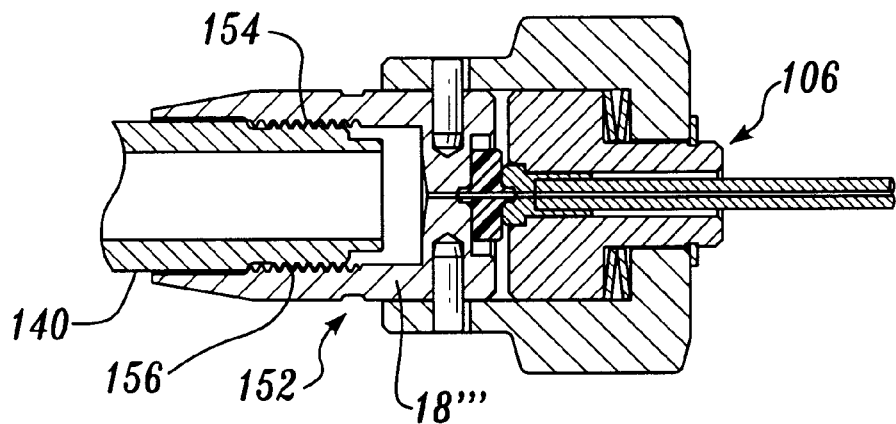
FIG. 9 is a longitudinal cross-sectional view of a third preferred embodiment of the quarter turn quick connect fitting of the present invention adapted for use as a column end fitting threadedly attached to the end of an external column.

FIG. 9 shows a third preferred embodiment of the present invention, adapted for use on the end of a column, which is similar to the second preferred embodiment previously described and illustrated in FIG. 8, except that the third preferred embodiment illustrated in FIG. 9 includes a first fitting 152 which is internally threaded. First fitting 152 is similar to first fitting 132 and so features of first fitting 152 that correspond to features of first fitting 132 are referred to with the same parts numbers as first fitting 132, but with the addition of a triple prime ('''). Thus, first fitting 152 includes a body 18''' having a proximal end 20''' and a distal end 22'''. Distal end 22''' is penetrated by two slots 30''' within which are inserted two dowels 28'''. Body 18''' defines a central passage 26''' having an internally threaded surface 154. Column end 140 has an externally threaded surface 156 to which first fitting 152 is threadably attached by means of internally threaded surface 154. First fitting 152 is connected to quarter turn nut 16, and quarter turn nut quick connect fitting 10 thereby assembled, as previously described. It will be appreciated that while the third preferred embodiment of the present invention, illustrated in FIG. 9, includes a second fitting 106 configured to receive a hollow tube set 104, an internally threaded second fitting 14 can instead be utilized.

Figure 10:
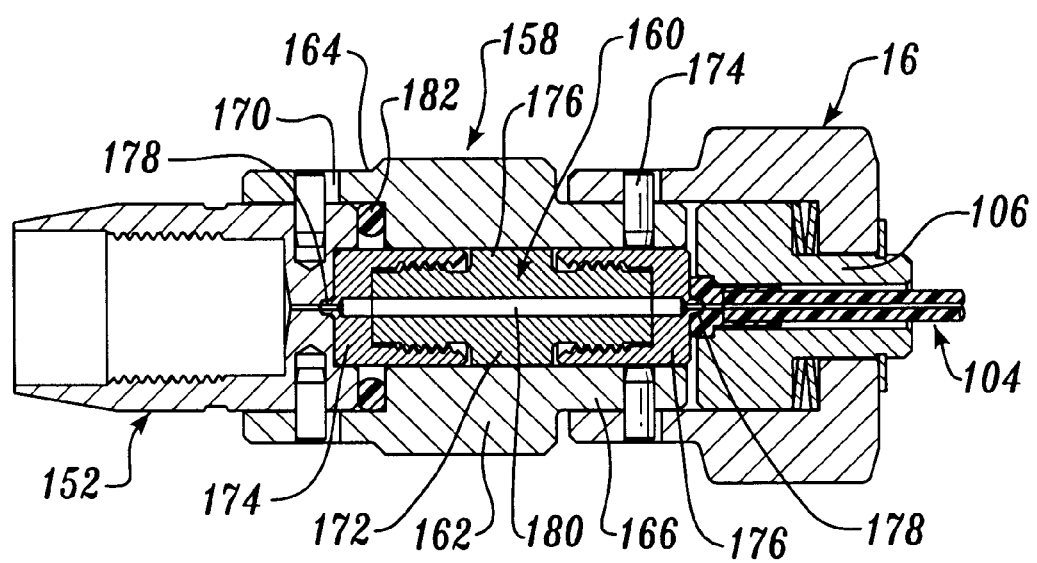
FIG. 10 is a longitudinal cross-sectional view of a fourth preferred embodiment of the quarter turn quick connect fitting of the present invention adapted to be threadedly attached to the end of a column and to include a precolumn filter housed within an adapter.

FIG. 10 shows a fourth preferred embodiment of the present invention, adapted for use on the end of a column, including a first fitting 152, a second fitting 106, a quarter turn nut 16 and a hollow tube set 104. Additionally, as shown in FIG. 10, the fourth preferred embodiment includes an adapter 158 configured to house a guard column 160, i.e., a filter. Adapter 158 includes a generally cylindrical body 162 having a proximal end 164 and a distal end 166. Adapter body 162 defines a central passage 168 of uniform diameter which opens into a cavity 169 within proximal end 164. Proximal end 164 of body 162 has a wider diameter than distal end 166 and is penetrated by two spiral grooves 170 which receive pins 28''' of first fitting 152.

Guard column 160 includes a body 172 which is assembled from a center piece 161 and two end pieces 163. End pieces 163 are threadably attached to center piece 161. Assembled body 160 has a first end 174 and a second end 176. A nipple 178 is centrally formed on each of first end 174 and second end 176. Guard column body 172 defines a central passage 180 that is of uniform diameter, except that central passage 180 narrows within nipples 178. One or more frits can be housed within the terminal ends of central passage 180, and additional filter medium such as a packed silica gel is contained therebetween, for filtering the fluid passing therethrough. When guard column 160 is inserted within central passage 168 of adapter 158, guard column second end 176 is flush with adapter distal end 166, while guard column first end 174 extends into cavity 169 of adapter proximal end 164. Alternately, the extended guard column could be housed within an extended nut housing in place of body 160.

The assembly of the fourth preferred embodiment of quarter turn nut quick connect fitting assembly 10 of FIG. 10 is now discussed in greater detail. Proximal end 164 of adapter 158 is coupled to distal end 22''' of first fitting 152 by inserting pins 28''' of first fitting 152 into spiral grooves 170 of adapter 158 and rotating adapter 158 through approximately 90° with respect to first fitting 152. When proximal end 164 of adapter body 162 is thus coupled to first fitting 152, a seal is formed between distal end 22''' of first fitting 152 and first end 174 of guard column body 172 as nipple 178, on first end 174 of guard column body 172, is compressed into recess 62''' on distal end 22''' of first fitting 152. Additionally, a seal is formed between distal end 22''' of first fitting 152 and proximal end 164 of adapter body 162 by means of an O-ring 182 coaxially mounted around the portion of guard column first end 174 protruding into adapter cavity 169. Distal end 166 of adapter 158 is coupled to quarter turn nut 16 by means of two radially projecting pins 184 that are seated within two slots 186 within adapter distal end 166. Pins 184 are inserted within spiral grooves 48 of quarter turn nut 16 and quarter turn nut 16 is rotated through approximately 90° with respect to adapter 158, thereby securely seating dowels 184 within enlarged areas 76 of spiral grooves 48. When adapter 158 is thus connected to quarter turn nut 16, nipple 178 on guard column second end 176 is compressed into recess 122 of head portion 116 of hollow tube set 104, thereby forming a seal. While the fourth preferred embodiment of the present invention is illustrated having a first fitting 152 and a second fitting 106, it will be appreciated that the fourth preferred embodiment can also include a first fitting 132 and a second fitting 12.

Figure 12:
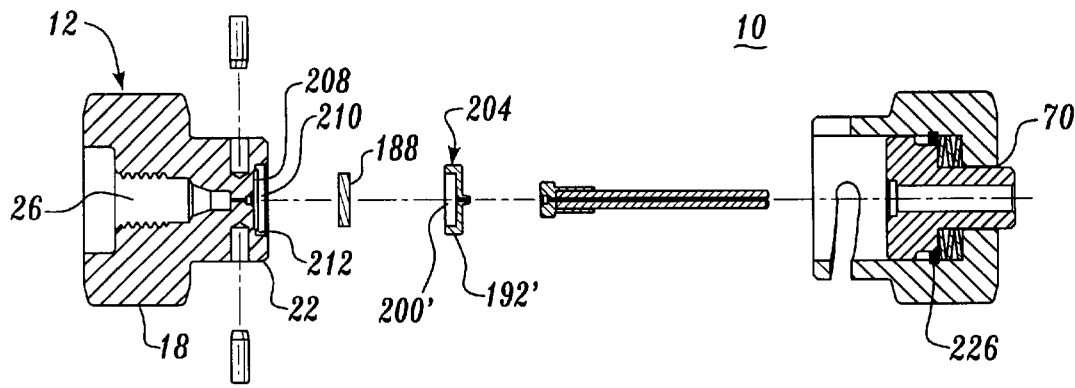
FIG. 12 is a longitudinal cross-sectional exploded view of a second configuration of a fifth preferred embodiment of the quarter turn quick connect fitting of the present invention including a frit, a frit ring and a sharply tapered sealing surface on the distal end of the first fitting.
Figure 13:
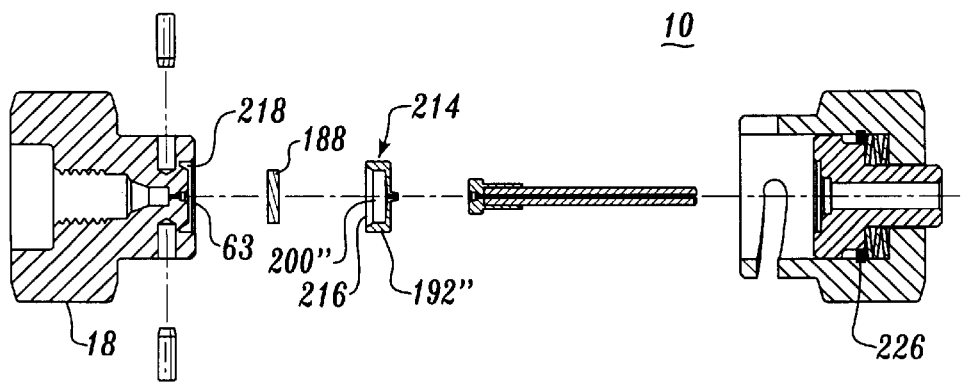
FIG. 13 is a longitudinal cross-sectional exploded view of a third configuration of a fifth preferred embodiment of the quarter turn quick connect fitting of the present invention including a frit and a frit ring having a beveled sealing surface.

While the fourth preferred embodiment of the present invention houses a guard column 160 and is intended to be attached to the inlet of an HPLC column, a fifth preferred embodiment shown in FIGS. 11–13 of the present invention can be inserted before or after any component of an HPLC system and includes a porous frit 188, that filters the fluid passing through the HPLC system. The fifth preferred embodiment of the present invention includes a quarter turn nut 16, a hollow tube set 104 where appropriate, and can include any of the first and second fitting configurations discussed previously.

FIG. 11 shows the disassembled, fifth preferred embodiment of the present invention including a first fitting 12 internally threaded to receive an externally threaded mating fitting, and a second fitting 106 configured to receive a hollow tube set 104. The fifth preferred embodiment includes a frit 188 which is composed of a sintered material, such as sintered titanium or sintered stainless steel. Frit 188 is seated within a frit ring 190 composed of an elastically deformable polymeric material, preferably a thermoplastic polymer such as polyetheretherketone. Frit ring 190 includes a body 192 having a first face 194 and a second face 196. A nipple 197 is centrally located on frit ring second face 196. Frit ring body 192 defines a central passage 198 that extends from nipple 197 to frit ring first face 194. Central passage 198 widens within frit ring body 192 to form annular cavity 200 that houses frit ring 188. Frit ring 190 also includes a circular groove 202 concentrically disposed around annular cavity 200.

The fifth preferred embodiment of the present invention is assembled as previously described, by sliding dowel pins 28 of first fitting 12 into spiral grooves 48 of quarter turn nut 16, and locking dowel pins 28 into place by turning quarter turn nut 16 through approximately 90° with respect to first fitting 12. At low operating pressure a seal is formed when first fitting 12 is connected to quarter turn nut 16 thereby compressing first face 194 of frit ring 190 into annular recess 63, and compressing nipple 197 into recess 122 of hollow tube set 104. At high operating pressure, fluid passing through assembled quick connect fitting 10 leaks into groove 202 and forces the portion of frit ring body 192 defining groove 202 to expand outward against first fitting body 18, and inward against frit 188, thereby forming a seal effective at high pressure.

FIG. 12 shows a second configuration of the fifth preferred embodiment of the present invention similar to the configuration previously described. The configuration shown in FIG. 12 includes a frit ring 204 that is identical to frit ring 190 except that frit ring 204 lacks circular groove 202. Corresponding features of frit ring 204 are referred to with the same parts numbers as frit ring 190, but with the addition of a prime ('). First fitting 12 is also specially adapted to form a seal with frit ring 204. Central passage 26 of first fitting 12 widens close to distal end 22 of first fitting 12 to form a first annular recess 208 set within a still larger second annular recess 210. Second annular recess 210 opens onto distal end 22 of first fitting 12. A sharply tapered annular ridge 212 is defined about the perimeter of the first annular recess 208 that is bordered by an annular groove. When quarter turn quick connect fitting 10 is assembled, as previously described, the portion of frit ring body 192' defining the outer circumference of annular cavity 200' is compressed against the ridge groove 212 to form a seal that is effective at low operating pressure. At high operating pressure, the portion of frit ring body 192' defining the outer circumference of annular cavity 200' expands outwards against first fitting body 18 to form a seal effective at high pressure.

FIG. 13 shows a third configuration of the fifth preferred embodiment of the present invention similar to the second configuration previously described. The configuration shown in FIG. 12 includes a frit ring 214 that is similar to frit ring 204. Corresponding features of frit ring 214 are referred to with the same parts numbers as frit ring 204, but with the addition of a double prime ("). The portion of frit ring body 192" defining the circumference of annular cavity 200" is beveled on frit ring first face 194" to form a sealing surface 216. When quarter turn quick connect fitting 10 is assembled, frit ring 214 is compressed and sealing surface 216 contacts a complementary, tapered sealing surface 218 around the circumference of annular recess 63. At high operating pressure, the portion of frit ring body 192" defining the outer circumference of annular cavity 200" expands outwards against first fitting body 18 to form a seal effective at high pressure.

Figure 14:
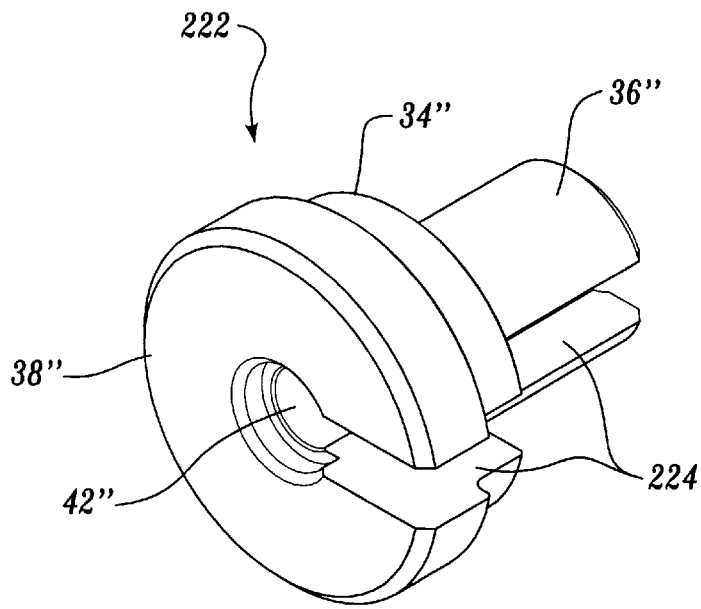
FIG. 14 is an isometric view of a second fitting of the present invention having a longitudinally slotted sidewall.

FIG. 14 shows a slotted second fitting 222 configured to permit the rapid and simple removal of second fitting 222 from within quarter turn nut 16, for example to permit the replacement of a hollow tube set 104 that has been damaged. Second fitting 222 is similar to second fitting 106 and corresponding features of second fitting 222 are referred to with the same parts numbers as second fitting 106, but with the addition of a double prime ("). Thus, second fitting 222 includes a unitary body 34" of generally cylindrical shape and having a proximal end 36" and a distal end 38", proximal end 36" being narrower than distal end 38". Second fitting body 34" defines a central passage 42" extending from proximal end 36" to distal end 38". Second fitting body 34" includes a longitudinal slot 224 extending from proximal end 36" to distal end 38" that completely penetrates one side of body 34". When second fitting 222 is removed from quarter turn nut cavity 66, slot 224 permits hollow tube set 104 to be removed by laterally sliding hollow tube set 104 out from second fitting 222. To permit easy removal, second fitting 222 is not fixedly retained within quarter turn nut 16. Instead, as shown in FIGS. 11, 12 and 13, retaining ring 226 is disposed within an annular groove defined internally within quarter turn nut cavity 66 to retain spring washers 44 when second fitting 222 is withdrawn. When second fitting 222 is removed from quarter turn nut cavity 66, and hollow tube set 104 slid laterally out through groove 224, quarter turn nut 16 can be separated from hollow tube set 104 by passing hollow tube set 104 through centrally-located hole 70 in quarter turn nut body 64. Hole 70 has a larger diameter than that of any part of hollow tube set 104.

Retaining ring 226 is seated within an annular that extends around the circumference of quarter turn nut cavity 66. The embodiment of quarter turn nut 16 having annular groove 228 can be used with any of the foregoing second fitting embodiments.

Figure 15:
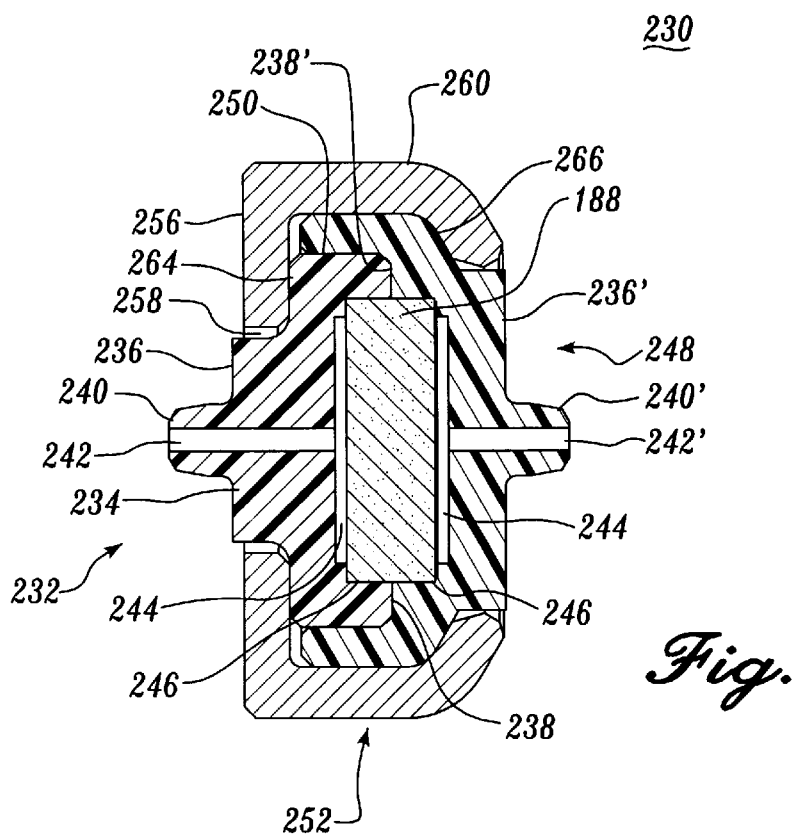
FIG. 15 is a longitudinal cross-sectional view of a filter element compatible with any of the embodiments of the quarter turn quick connect fitting of the present invention, the filter element including a frit, a small frit ring, a large frit ring and a filter housing.

FIG. 15 shows an encapsulated filter element 230 that can be used with any of the foregoing embodiments of the quarter turn quick connect fitting of the present invention. Thus, filter element 230 includes a frit 188 which is composed of a sintered material, such as sintered titanium or sintered stainless steel. Frit 188 is seated within an annular small frit ring 232 composed of a elastically deformable polymeric material, such as a thermoplastic or elastomeric material. Small frit ring 232 includes a body 234 having a first face 236 and a second face 238. A nipple 240 is centrally located on first face 236. Small frit ring body 234 defines a central passage 242 that extends from first face nipple 240 to frit ring second face 238. Central passage 242 widens close to frit ring second face 238 to form first annular portion 244 which, in turn, widens to form second annular portion 246 which opens onto frit ring second face 238 and receives a portion of frit 188.

Once frit 188 is seated within second annular portion 246 of small frit ring 232, assembled frit 188 and small frit ring 232 are then housed within a large frit ring 248. Large frit ring 248 is similar to small frit ring 232, so corresponding elements will be identified with the same number, but with the addition of a prime ('). Thus, large frit ring 248 includes a body 234' having a first face 236' and a second face 238'. A nipple 240' is centrally located on first face 236'. Large frit ring body 234' defines a central passage 242' that extends from first face nipple 240' to large frit ring second face 238'. Central passage 242' widens close to large frit ring second face 238' to form first annular portion 244' which, in turn, widens to form second annular portion 246' which again widens to form third annular portion 250 which opens onto large frit ring second face 238'. Small frit ring 232 and frit 188, retained within small frit ring second annular portion 246, are housed within large frit ring 248 such that the portion of frit 188 exterior to small frit ring second face 238 is received within large frit ring 248 second annular portion 246', and a portion of small fit ring 232, including at least second face 238, is received within third annular portion 250.

Small frit ring 232 and large frit ring 248 are held together by a cup shaped metallic filter housing 252. Filter housing 252 includes an annular end face 256 penetrated by a centrally-located aperture 258 and surrounded by a tubular side wall 260. To assemble filter element 230, small frit ring first face 236 is inserted into aperture 258 of filter housing end face 256 until filter housing end face 256 engages a shoulder 264 defined by small frit ring first face 236. Consequently, assembled small frit ring 232, large frit ring 248 and frit 188 are surrounded by side wall 260. The edge of sidewall 260 is then swaged around large frit ring 248, to secure and compress all elements together to form a sealed assembly. Small frit ring 232 and large frit ring 248 each thus define an inlet or outlet 242, 242' which flows into chamber 24, 244' facing one side of the frit 188.

Figure 16:
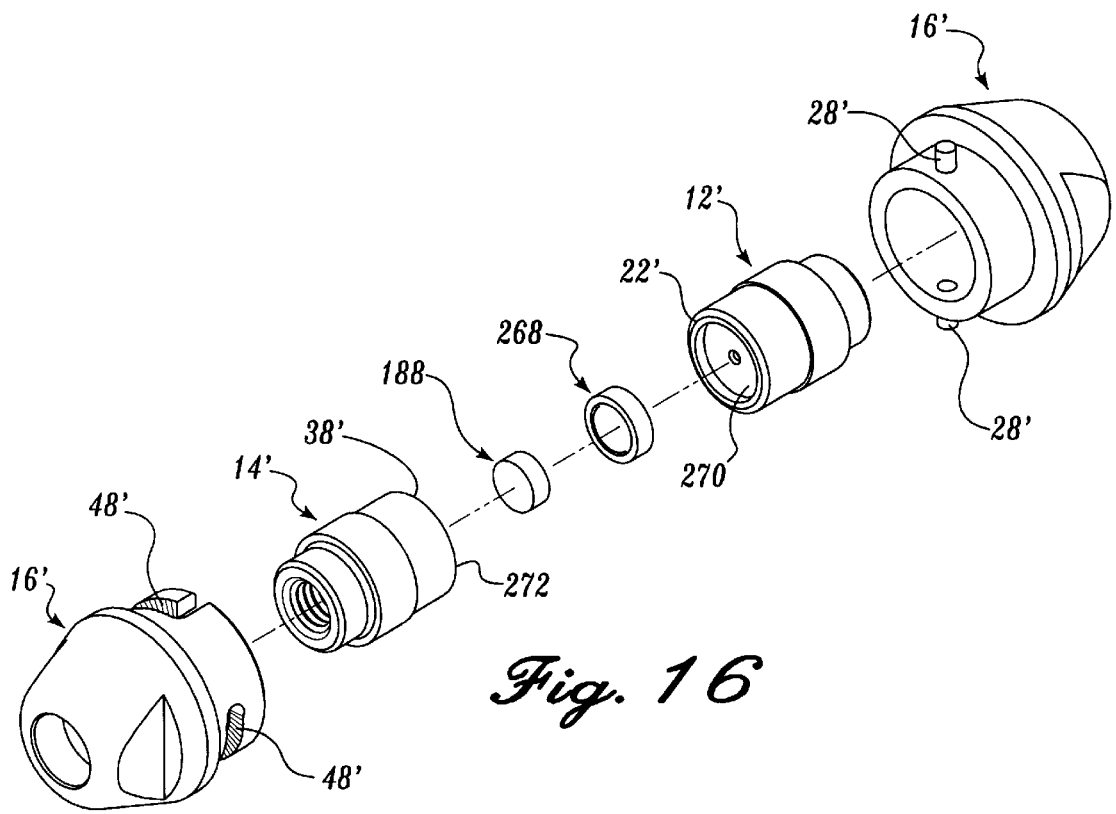
FIG. 16 is a longitudinal cross-sectional exploded view of a sixth preferred embodiment of the quarter turn quick connect fitting of the present invention, including a frit and a compressible frit ring.

FIG. 16 shows a sixth preferred embodiment of the quarter turn quick connect fitting 10 of the present invention in which a seal is formed within the fitting solely by means of an annular frit ring having a predetermined degree of compressibility. The sixth preferred embodiment of the quarter turn quick connect fitting 10 of the present invention, shown in FIG. 16, is similar to the first preferred embodiment of the quarter turn quick connect fitting 10 of the present invention, so corresponding elements will be identified with the same number, but with the addition of a prime ('). The sixth preferred embodiment of the quarter turn quick connect fitting 10 of the present invention, shown in FIG. 16, includes a first fitting 12' and a second fitting 14' housed within a slotted quarter turn nut 16'. Unlike the first fitting 12' of the first preferred embodiment of the quarter turn quick connect fitting 10 of the present invention, first fitting 12' of the sixth preferred embodiment is located within a separate pinned quarter turn nut 16'. The sixth preferred embodiment of the quarter turn quick connect fitting 10 of the present invention also includes a frit 188 which is housed within a compressible frit ring 268. When the sixth preferred embodiment of the present invention is assembled, frit ring 268, including frit 188, is seated within a cavity formed between first fitting 12' and second fitting 14' by an annular recess 270, defined by first fitting distal end 22', and an annular recess 272, defined by second fitting distal end 38'.

When the sixth preferred embodiment of the present invention is assembled, by inserting dowel pins 28', of pinned quarter turn nut 16' housing first fitting 12', into spiral grooves 48', of slotted quarter turn nut 16' housing second fitting 14', and rotating one or both quarter turn nuts 16' through approximately 90° with respect to each other, frit ring 268 is compressed, thereby forming a seal between the first and second fittings and around frit 188. Thus, the sixth preferred embodiment of the quarter turn nut quick connect fitting 10 of the present invention does not require an additional, axial spring force, such as that provided by washers 44 in the first preferred embodiment, to form a seal around frit 188. While the sixth preferred embodiment of the present invention shown in FIG. 16 includes two quarter turn nuts 16' within which first fitting 12' and second fitting 14' are separately housed, it will be appreciated that the sixth preferred embodiment of the present invention is also operable where one or both of the first fitting 12' or the second fitting 14' are not housed within a separate quarter turn nut 16', instead including pins or an integral slotted annular sleeve forming the nut.

Figure 17:
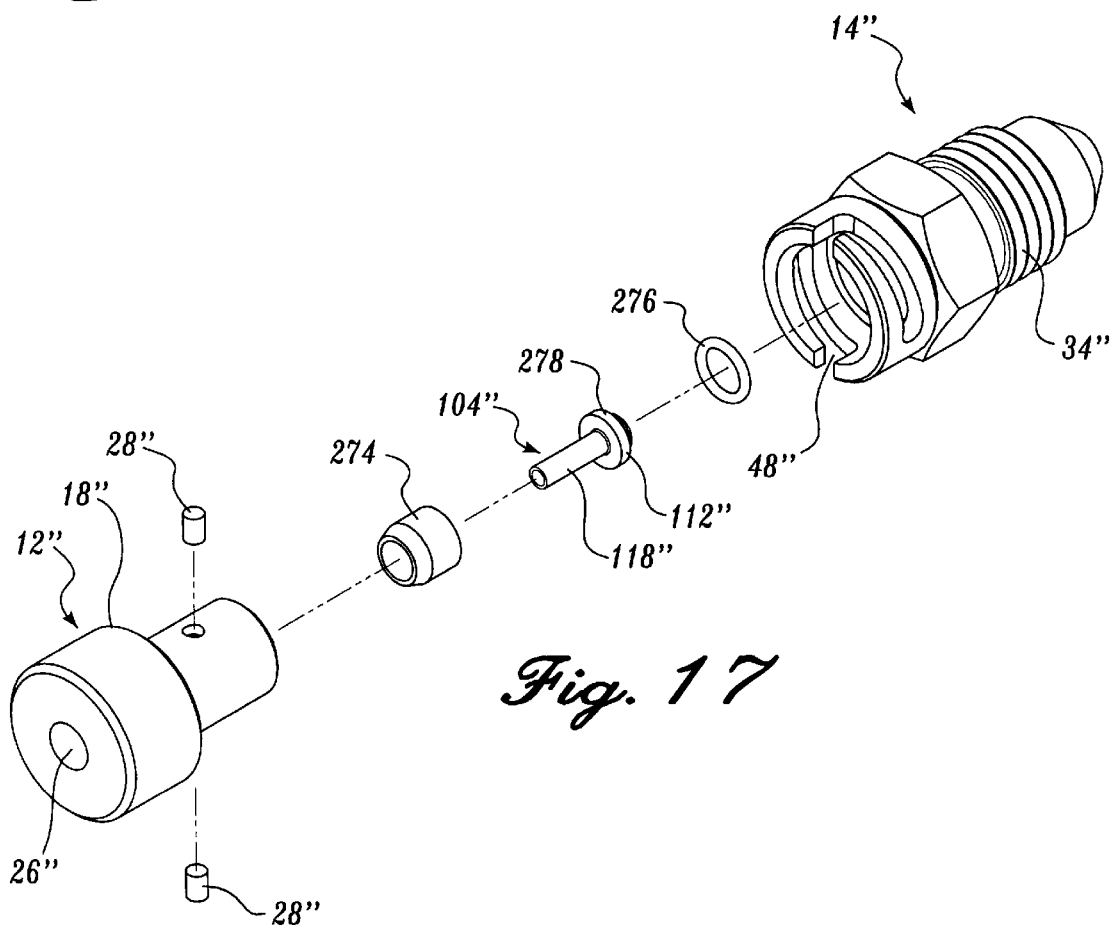
FIG. 17 is a longitudinal cross-sectional exploded view of a seventh preferred embodiment of the quarter turn quick connect fitting of the present invention, including a hollow sleeve, a hollow tube set and an annular sealing member.

FIG. 17 shows a seventh preferred embodiment of the quarter turn quick connect fitting 10 of the present invention in which a seal is formed within fitting 10 solely by means of an annular sealing member. The seventh preferred embodiment of the quarter turn quick connect fitting 10 of the present invention is similar to the first preferred embodiment of the quarter turn quick connect fitting 10 of the present invention, so corresponding elements will be identified with the same number, but with the addition of a double prime ("). Thus, the seventh preferred embodiment of the quarter turn quick connect fitting 10 of the present invention includes a first fitting 12" and a second fitting 14" but, unlike the first preferred embodiment of the quarter turn quick connect fitting 10 of the present invention, second fitting 14" is not housed within a separate quarter turn nut 16" defining grooves 48" for receiving dowels 28" of first fitting 12". Instead, second fitting 14" is of unitary construction and includes an integral nut defined by sleeve extension 34" including grooves 48" for receiving dowels 28" of first fitting 12". Additionally, the seventh preferred embodiment of the quarter turn quick connect fitting 10 of the present invention includes a hollow tube set 104", a hollow sleeve 274 and an annular sealing member 276, such as that disclosed in U.S. Pat. No. 5,669,637 to Martin et al. Hollow tube set 104" includes a head 112" and a stem 118" that extends longitudinally from the center of head 112" and has a smaller diameter than head 112". Head 112" narrows in the portion farthest from stem 118" to form a recessed sealing surface 278 for engaging annular sealing member 276.

The end of a tubular conduit (not shown) can be slidably inserted through sleeve 274 and onto stem 118", with the sleeve 274 then slid down to contact head 112". The tubular conduit is then compressed between sleeve 274 and tube set 104" upon mating. First fitting 12" and second fitting 14" are mated by inserting dowel pins 28" of first fitting 12" into spiral grooves 48" of second fitting 14", and rotating second fitting 14" through approximately 90° with respect to first fitting 12". Annular sealing member 276 is compressed within assembled quarter turn quick connect fitting 10, thereby forming a seal around head 112".

While the preferred embodiment of the invention and alternate embodiments thereof have been illustrated and described, it will be appreciated that various changes can be made therein without departing from the spirit and scope of the invention. Thus by way of nonlimiting example, the quarter turn quick connect fitting assemblies can be variously adapted, based on the disclosures contained herein, to permit rapid selective mating of chemical analytical equipment sealed to withstand liquids under pressure such as: tube sets, unions, tees, column end fittings, column adapters, detector bulkhead fittings and adapters, flow cell fittings, detector waste lines, back pressure regulators, guard columns, in-line filters, guard column cartridges, injector sample loops and rotor systems, auto sampler syringes, needles and valves, pump fittings, filters, pulse dampeners, mixers, tees, prime/purge valves, low/high pressure valves, check valves, cartridge check valves, pumpheads and plungers, solvent lines and mixers, and solvent reservoir filter and degassing units. Thus it is intended that the scope of letters patent granted hereon be limited only by the scope of the appended claims.

The embodiments of the invention in which an exclusive property or privilege is claimed are defined as follows:

1. A quick connect high pressure liquid chromatograph fitting assembly for coupling first and second analytical miniature fluid conduits, comprising:
    (a) a first fitting defining a central passage adapted for receiving therein a first analytical miniature fluid conduit defining an internal diameter of no greater than 0.040 inch, the first fitting defining at least one first radial engaging surface;
    (b) a second fitting defining a central passage adapted for receiving therein a second analytical miniature fluid conduit defining an internal diameter of no greater than 0.040 inch,
    (c) a polymeric sealing element;
    (d) a nut provided on the second fitting, wherein the nut defines at least one second radial engaging surface, wherein the nut is selectively rotatable less than 360° relative to the first fitting to engage the first and second engaging surfaces to compress and seal the polymeric sealing element between the first and second fittings for fluid flow communication between the first and second analytical miniature fluid conduits; and
    (e) a biasing member engageable between the first and second fittings to bias the second fitting towards the first fitting upon engagement of the first and second fittings, said quick connect high pressure liquid chromatograph fitting assembly defining a zero dead volume fluid path for coupling said first and said second analytical miniature fluid conduits and being capable of withstanding a maximum internal fluid pressure of greater than 6000 p.s.i..

2. The fitting assembly of claim 1, wherein one of the first and second radial engaging surfaces comprises a radially projecting pin and the other of the first and second radial engaging surfaces comprises a groove for selectively and slidably receiving the pin.

3. The fitting assembly of claim 2, wherein the first radial engaging surface comprises the radially projecting pin and the second radial engaging surface comprises the groove.

4. The fitting assembly of claim 3, wherein the groove comprises a spiral groove.

5. The fitting assembly of claim 4, comprising a plurality of pins projecting radially from the first fitting to selectively engage with a plurality of spiral grooves defined in the nut.

6. The fitting assembly of claim 5, wherein the first and second fitting are securely engaged and sealed with approximately a 90° turn of the nut relative to the first fitting.

7. The fitting assembly of claim 6, further comprising an aperture defined in the nut and at least one indicia defined in one of the first and second fittings whereby the indicia is exposed through the aperture when the first and second fittings are in one of a secured or unsecured configuration, and upon rotation of the nut to the other of the secured or unsecured configuration the indicia is obscured by the nut.

8. The fitting assembly of claim 4, wherein the spiral groove defines a contoured locking portion thereof for selective locking of the pin in the groove.

9. The fitting assembly of claim 8, wherein the locking portion defines an inversely angled surface of the groove.

10. The fitting assembly of claim 4, wherein the groove perforates the nut to define a spiral slot.

11. The fitting assembly of claim 1, wherein the first and second fittings are secured together with approximately a 90° turn of the nut relative to the first fitting.

12. The fitting assembly of claim 1, further comprising a selective locking portion of one of the first and second radial engaging surfaces for selectively locking against the other of the first and second radial engaging surfaces when the nut is rotated to a locked position.

13. The fitting assembly of claim 1, wherein the polymeric sealing element is sealed between the first and second fittings to withstand liquid pressure of at least 300 psi without leakage.

14. The fitting assembly of claim 1, wherein the sealing element comprises an annular polymeric member defining a central passage therethrough.

15. The fitting assembly of claim 14, wherein the sealing element defines first and second sealing nipples defined about first and second ends of the central passage that engage with and seal against corresponding first and second sealing recesses defined in the first and second fittings.

16. The fitting assembly of claim 1, wherein the first and second fluid conduits are placed in substantially zero-dead volume for communication when the first fitting is secured to the second fitting.

17. The fitting assembly of claim 1, wherein the biasing member comprises a spring engageable between the nut and the second fitting to bias the second fitting towards the first fitting upon engagement of the first and second fittings.

18. The fitting assembly of claim 17, wherein the spring comprises at least one annular spring washer received upon the second fitting and captured between the second fitting and the nut.

19. The fitting assembly of claim 1, wherein at least one of the first and second fittings includes an internally threaded central passage for engaging the corresponding first or second fluid conduit therein.

20. The fitting assembly of claim 1, further comprising an annular tube set slidably received within the central passage of one of the first or second fittings, wherein the tube set includes an annular head captured between the first and second fittings and a tubular stem projecting from the first or second fitting in which it is received.

21. The fitting assembly of claim 20, wherein the sealing element is received between the head of the tube set and the other of the first and second fittings.

22. The fitting assembly of claim 21, wherein the other of the first and second fittings defines a contoured sealing surface for sealing against the sealing element.

23. The fitting assembly of claim 21, wherein the sealing element defines an annular sealing contour for sealing against the other of the first and second fittings.

24. The fitting assembly of claim 1, further comprising a tube set receivable within the central passage of one of the first and second fittings, the tube set capable of receiving the corresponding first or second fluid conduit therein, wherein the one of the first and second fittings defines a longitudinal slot for lateral insertion and removal of the tube set.

25. The fitting assembly of claim 1, wherein the nut is separately formed and rotatably mounted on the second fitting.

26. A quick connect fitting assembly for coupling first and second analytical miniature fluid conduits, comprising:
   (a) a first fitting defining a central passage for receiving a first analytical miniature fluid conduit therein;
   (b) a second fitting defining a central passage for receiving a second analytical miniature fluid conduit therein;
   (c) a polymeric sealing element defining first and second ferrule ends for flow-through sealing to the first and second analytical miniature conduits, respectively; and
   (d) a nut provided on the second fitting, wherein one of the first fitting and nut defines at least one radial protrusion and the other of the first fitting and nut defines at least one corresponding radial engaging surface, wherein the nut is selectively rotatable less than 360° relative to the first fitting to engage the protrusion with the engaging surface to compress the polymeric sealing element between the first and second fittings for fluid flow communication between the first and second analytical miniature fluid conduits, said quick connect fitting assembly defining a zero dead volume fluid path for coupling said first and said second analytical miniature fluid conduits and using capable of withstanding a maximum internal fluid pressure of greater than 6000 p.s.i..

27. The fitting assembly of claim 26 wherein the first and second fittings are adapted to receive a first miniature analytical fluid conduit and a second miniature analytical fluid conduit, respectively, each of said first and second miniature analytical fluid conduits defining an internal diameter of no greater than 0.040 inch.

28. A quick connect high pressure liquid chromatograph fitting assembly for coupling first and second analytical miniature fluid conduits, comprising:
   (a) a first tubular fitting for coupling to a first analytical miniature fluid conduit, the first fitting defining at least one first radial engaging surface;
   (b) a second tubular fitting for coupling to a second analytical miniature fluid conduit;
   (c) a nut provided on the second fitting, wherein the nut defines at least one second radial engaging surface, wherein the nut is selectively rotatable with a single hand motion relative to the first fitting to engage the first and second engaging surfaces to create a secure seal capable of withstanding liquid pressure of at least 6000 p.s.i. between the first and second fittings for substantially zero dead volume fluid flow communication between the first and second analytical miniature fluid conduits, and
   (d) a biasing member engageable between the first and second fittings to bias the second fitting towards the first fitting upon engagement of the first and second fittings.

29. The fitting assembly of claim 28 wherein the first and second tubular fittings are adapted to receive a first miniature analytical fluid conduit and a second miniature analytical fluid conduit, respectively, each of said first and second miniature analytical fluid conduits defining an internal diameter of no greater than 0.040 inch.

30. A quick connect high pressure liquid chromatograph fitting assembly for coupling first and second analytical miniature fluid conduits, comprising:
   (a) a first fitting defining a central passage for receiving a first analytical miniature fluid conduit therein;
   (b) a second fitting defining a central passage for receiving a second analytical miniature fluid conduit therein; and (c) a nut provided on the second fitting, wherein one of the first fitting and nut defines at least one radial protrusion and the other of the first fitting and nut defines at least one corresponding groove defining a locking surface, wherein the nut is selectively movable in, the absence of rotation exceeding 360° relative to the first fitting to create a locking engagement between the protrusion and the locking surface of the groove to create a secure selectively locked seal capable of withstanding liquid pressure of at least 6000 p.s.i. between the first and second fittings for substantially zero dead volume fluid flow communication between the first and second analytical miniature fluid conduits.

31. The fitting assembly of claim 30 wherein the first and second fittings are adapted to receive a first miniature analytical fluid conduit and a second miniature analytical fluid conduit, respectively, each of said first and second miniature analytical fluid conduits defining an internal diameter of no greater than 0.040 inch.

32. A quick connect high pressure liquid chromatograph fitting assembly for coupling first and second analytical miniature fluid conduits, comprising:

(a) a first fitting defining a central passage for receiving a first analytical miniature fluid conduit therein;

(b) a second fitting defining a central passage for receiving a second analytical miniature fluid conduit therein;

(c) a nut provided on the second fitting, wherein one of the first fitting and nut defines at least one radial protrusion and the other of the first fitting and nut defines at least one corresponding radial locking surface, wherein the nut is selectively movable with a single hand motion relative to the first fitting to create a locking engagement between the protrusion and the locking surface of the groove to create a secure selectively locked seal capable of withstanding liquid pressure of at least 6000 p.s.i. between the first and second fittings for substantially zero dead volume fluid flow communication between the first and second analytical miniature fluid conduits; and (d) auto adjustment means for automatically adjusting the longitudinal positioning of the first fitting relative to the second fitting when the nut is moved into locking engagement.

33. The fitting assembly of claim 32 wherein the first and second fittings are adapted to receive a first miniature analytical fluid conduit and a second miniature analytical fluid conduit, respectively, each of said first and second miniature analytical fluid conduits defining an internal diameter of no greater than 0.040 inch.

34. A quick connect fitting assembly for coupling first and second analytical miniature fluid conduits, comprising:

(a) a first tubular fitting for coupling to a first analytical miniature fluid conduit, and acting against a stop defined on the first analytical miniature fluid conduit to axially locate the first analytical miniature fluid conduit prior to connection, the first fitting defining at least one first radial engaging surface;

(b) a second tubular fitting for coupling to a second analytical miniature fluid conduit and acting against a stop defined on the second analytical miniature fluid conduit to axially locate the second analytical miniature fluid conduit prior to connection;

(c) a polymeric sealing element;

(d) a nut provided on the second fitting, wherein the nut defines at least one second radial engaging surface, wherein the nut is selectively quick connectable to the first fitting to engage the first and second engaging surfaces to compress and seal the polymeric sealing element between the first and second fittings to create a secure selectively locked seal capable of withstanding a maximum liquid pressure of about 6000 p.s.i. for substantially zero dead volume fluid flow communication between the first and second analytical miniature fluid conduits, and (e) a biasing member engageable between the first and second fittings to bias the second fitting towards the first fitting upon engagement of the first and second fittings.

35. The fitting assembly of claim 34 wherein the first and second tubular fittings are adapted to receive a first miniature analytical fluid conduit and a second miniature analytical fluid conduit, respectively, each of said first and second miniature analytical fluid conduits defining an internal diameter of no greater than 0.040 inch.

36. A quick connect high pressure liquid chromatograph fitting assembly for coupling first and second analytical miniature fluid conduits, comprising:

(a) a first tubular fitting for coupling to a first analytical miniature fluid conduit, and acting against a stop defined on the first analytical miniature fluid conduit to axially locate the first analytical miniature fluid conduit prior to connection;

(b) a second tubular fitting for coupling to a second analytical miniature fluid conduit and acting against a stop defined on the second analytical miniature fluid conduit to axially locate the second analytical miniature fluid conduit prior to connection;

(c) a polymeric sealing element;

(d) a retainer mountable about the first and second fittings to engage engaging surfaces defined by the first and second fittings to selectively quick connect the first fitting to the second fitting to compress and seal the polymeric sealing element between the first and second fittings to withstand fluid pressure of at least 6000 p.s.i. for substantially zero dead volume fluid flow communication between the first and second analytical miniature fluid conduits; and (e) a biasing member engageable between the first and second fittings to bias the first and second fittings together.

37. The fitting assembly of claim 36 wherein the first and second tubular fittings are adapted to receive a first miniature analytical fluid conduit and a second miniature analytical fluid conduit, respectively, each of said first and second miniature analytical fluid conduits defining an internal diameter of no greater than 0.040 inch.

* * * * *